US006319907B1

(12) United States Patent
Ferguson

(10) Patent No.: US 6,319,907 B1
(45) Date of Patent: Nov. 20, 2001

(54) WOUND HEALING

(75) Inventor: Mark W. J. Ferguson, Derbyshire (GB)

(73) Assignee: Renovo Limited, Manchester (GB)

( * ) Notice: Subject to any disclaimer, the term of this patent is extended or adjusted under 35 U.S.C. 154(b) by 0 days.

(21) Appl. No.: 09/367,262

(22) PCT Filed: Feb. 13, 1998

(86) PCT No.: PCT/GB98/00316

§ 371 Date: Aug. 25, 1999

§ 102(e) Date: Aug. 25, 1999

(87) PCT Pub. No.: WO98/35695

PCT Pub. Date: Aug. 20, 1998

(30) Foreign Application Priority Data

Feb. 13, 1997 (GB) .................................................. 9702943

(51) Int. Cl.[7] .......................... A61K 38/28; A61K 38/00; A01N 37/18; C07K 14/00; C07K 1/00
(52) U.S. Cl. ................................. 514/44; 514/2; 530/300; 530/350
(58) Field of Search ............................. 435/320.1; 514/2, 514/44; 530/300, 350; 800/4, 13, 18

(56) References Cited

U.S. PATENT DOCUMENTS 5,972,335 * 10/1999 Ferguson et al. .................. 424/141.1
6,074,840 * 6/2000 Bonadio et al. .................... 435/69.1

FOREIGN PATENT DOCUMENTS

| WO 9108291 | 6/1991 | (WO) . |
|---|---|---|
| WO-91/ 08291- | * 6/1991 | (WO) . |
| WO 9217206 | 10/1992 | (WO) . |
| WO 9409812 | 5/1994 | (WO) . |
| WO-94/ 09812- | * 5/1994 | (WO) . |
| WO 95/26203 | 10/1995 | (WO) . |

OTHER PUBLICATIONS

Grainger et al., Release and activation of platelet latent TGF–beta in blood clots during dissolution with plasmin, 1995, Nature, vol. 1, pp. 932–937.*
Mountain et al., Gene therapy: the first decade, Tibtech, vol. 18, Mar. 2000, pp. 119–128.*
Mullins et al. J. Clin Invest. 98(11): S37–S40, Dec. 1996.*
Palmiter, RD. Ann Rev. Genet. 20: 465–499, 1986.*
Suzuki et al. Human Gene Therapy. 9: 1223–1231, May 1998.*
Verma et al. Nature. 389: 239–242, Sep. 1997.*
Ledley, F.D. Pharmaceutical Research. 13: 1595–1614, Dec. 1996.*
Sha et al, "Identification and Analysis of Discrete Functional Domains in the Pro Region of Pre–Pro–Transforming Growth Factor Beta 1", The Journal of Cell Biology 114(4):827–839 (1991).
Ashcroft et al, "Estrogen accelerates cutaneous wound healing associated with an increase in TGF–β1 levels", Nature Medicine 3(11):1209–1215 (1997).
Ashcroft et al, "Topical Estrogen Accelerates Cutaneous Wound Healing in Aged Humans Associated with an Altered Inflammatory Response", American Journal of Pathology 155(4):1137–1146 (1999).
Bottinger et al. "The recombinant proregion of transforming growth factor β1 (Latency–associated peptide) inhibits active transforming growth factor β1 in transgenic mice", Proc. Natl. Acad. Sci. USA 93:5877–5882 (1996).
Kovacina et al. "Interactions of Recombinant and Platelet Transforming Growth Factor–β1 Precursor With the Insulin––Like Growth Factor II/Mannose 6–Phosphate Receptor", Biochemical and Biophysical Research Communications 160(1):393–403 (1989).
Dennis and Rifkin, "Cellular activation of latent transforming growth factor β requires binding to the cation–independent mannose 6–phosphate/insulin–like growth factor type II receptor", Proc. Natl. Acad. Sci. USA 88:580–584 (1991).
Sato et al, "The Mechanism for the Activation of Latent TGF–β during Co–culture of Endothelial Cells and Smooth Muscle Cells: Cell–type Specific Targeting of Latent TGF–β to Smooth Muscle Cells", The Journal of Cell Biology 123(5):1249–1254 (1993).

* cited by examiner

Primary Examiner—Deborah J. R. Clark
Assistant Examiner—Eleanor Sorbello
(74) Attorney, Agent, or Firm—Nixon & Vanderhye P.C.

(57) ABSTRACT

A composition for use in the treatment of wounds to inhibit scar tissue formation during healing is disclosed, comprising an effective activity-inhibiting amount of a growth factor neutralizing agent or agents specific against only fibrotic growth factors together with a pharmaceutically acceptable carrier. The method of preparation of said composition and method of administering the composition to a host suffering from tissue wounding is also disclosed.

14 Claims, No Drawings

WOUND HEALING

The present invention relates to the healing of wounds.

Wound healing in adult tissues is a complicated reparative process. In skin for example the healing process involves the recruitment of a variety of specialised cells to the site of the wound, extracellular matrix and basement membrane deposition, angiogenesis, selective protease activity and re-epithelialisation.

There is a need to provide medicaments that promote the healing of wounds. For example, it is often desirable to increase the rate of healing in the case of acute wounds (such as penetrative injuries, burns, nerve damage or even wounds resulting from elective surgery), chronic wounds (such as diabetic, venous and decubitus ulceration) or for generally healing compromised individuals (for example the elderly). In these examples, the wounds can severely influence quality of life or even result in death and therefore the rate of healing often needs to be increased as much as is clinically possible.

The term "wounds" as used herein is exemplified but not limited to injuries to the skin. Other types of wound can involve damage, injury or trauma to an internal tissue or organ such as the lung, kidney, heart, gut, tendons or liver.

There have been several recent developments in the wound healing field. Some of these developments revolve around the recent understanding that growth factors are intimately involved in the repair of wounded tissue. In particular, members of the Transforming growth Factor β (TGF-β) superfamily have been found to play an important role in wound healing. At least 25 molecules are known to be members of the TGF-β superfamily. These include a number of cytokines such as TGF-βs 1 to 5, the DVR group (e.g. dpp and Vg1), Bone Morphogenetic Proteins, Nodal, Activin and Inhibin.

TGF-β (and other members of the superfamily) are secreted from cells as a pro-protein which is known as latent TGF-β. The pro-protein consists of an N terminal Latency Associated peptide (LAP) and the TGF-β and is referred to as the Small Latent Complex. Additionally the Small Latent Complex can bind to another peptide (derived from a different gene) of variable size called Latent TGF-β Binding Protein (LTBP) in which case the entire complex is known as the Large Latent TGF-β Complex.

Upon secretion of the pro-protein into the extracellular environment, proteolytic cleavage of LAP (and LTBP) from TGF-β can occur. However, TGF-β may remain non-covalently associated with LAP. TGF-β is activated when it is caused to be dissociated from the LAP. This dissociation may be coordinated at a mannose-6-phosphate/Insulin Like Growth Factor II receptor (M6P-R) and involve proteases such as plasmin, the substrates being associated at the cell surface by tissue transglutaminase. Free radicals and reactive oxygen species can also activate TGF-β by causing dissociation from the LAP.

TGF-β (particularly TGF-β1 and TGF-β2) promotes wound healing but is also associated with increased scar formation and fibrosis. In fact, clinical interest in the modulation of TGF-β has been associated with inhibiting its activity in order to reduce scar formation (although this may compromise the rate of wound healing). For instance, WO 92/17206 discloses compositions which inhibit the activity of TGF-β1 and TGF-β2 and are particularly beneficial for reducing scar formation.

Another development in the field involves the use of mannose-6-phosphate for use in treating fibrotic disorders associated with elevated levels of TGF-β (GB 2,265,3 10). Mannose-6-phosphate is believed competitively to interfere with the liberation of TGF-β from LAP at the M6P-R thereby inhibiting TGF-β activation and preventing fibrosis or scarring.

WO 91/08291 and WO 94/09812 relate to the role of LAP in modulating TGF-β activity and disclose methods of producing LAP and large latent TGF-β respectively. These documents also provide uses of LAP for antagonising or neutralising TGF-β activity by binding to TGF-β and reverting it back to a latent state. It is claimed that a consequence of this antagonism is to reduce scarring following wounding.

According to a first aspect of the present invention there is provided the use of Latency Associated Peptide, or a functional analogue thereof, for the manufacture of a medicament for increasing the rate of wound healing.

According to a second aspect of the present invention, there is provided a method of increasing the rate of wound healing comprising applying to the site of the wound a therapeutically effective amount of Latency Associated Peptide or functional analogue thereof.

The Latency Associated Peptide (LAP) used according to the invention is the N terminal region of the pro-proteins of the Transforming Growth factor β (TGF-β) superfamily of molecules, the said region being capable of maintaining at least one of the members of the TGF-β superfamily in a latent state. It is preferred that the LAP is capable of maintaining a TGF-β in a latent state and most preferred that the LAP will maintain TGF-β1 and/or TGF-β2 in a latent state.

In accordance with the invention, the inventors have established that LAP may be used to increase the rate at which a wound will heal. For example, in skin, we have found that LAP, or a functional analogue thereof, increases the rate of dermal healing (i.e. an open wound closes quicker when LAP is applied to the wound). This increase in the rate of healing can be further characterised by any of: an increase in the recruitment of a variety of specialised cells to the site of the wound (fibroblasts, leukocytes etc), an increase in extracellular matrix and basement membrane deposition, increased angiogenesis, increased selective protease activity and quicker re-epithelialisation.

This is a surprising development in the light of conventionally accepted interactions of TGF-β and LAP which are discussed above. According to the teaching of the prior art, LAP would be expected to antagonise or neutralise the effects of TGF-β and thereby reduce scarring and/or fibrosis. Conventionally such an effect would also be expected to result in a reduction in the rate of wound healing (e.g. slower closing of a incisonal wound of the skin).

The invention has been based on the inventors' studies which have shown that LAP, contrary to expectations, increases the rate of wound healing. These findings led to the realisation that LAP actually promotes the wound healing effects of TGF-β (and related molecules) and, at least with respect to wound healing, does not neutralise or antagonise TGF-β as suggested by WO 91/08291.

Although the inventors do not wish to be constrained by any hypothesis, they believe it is possible that the mechanism by which LAP is effective in increasing the rate of wound healing is by binding to TGF-β and protecting it from proteolytic degradation. This results in the sequestration of the active TGF-β (particularly TGF-β1 and TGF-β2) which is normally present during wound healing. This sequestered TGF-β may then act as a reserve which may be released into the wound and will effectively increase the half life of TGF-β over which time it promotes healing.

We have found that administration of LAP offers advantages over the use of exogenous TGF-β for increasing the rate of wound healing. Administration of exogenous doses of TGF-β can lead to inappropriately high localised concentrations of TGF-β which, as TGF-β increases the rate of wound healing and induces scarring or fibrosis, can cause unacceptable scarring or fibrosis. Administration of LAP, or a functional analogue thereof, has no such adverse effect and only modulates the activity of endogenously present TGF-β. Thus LAP, or a functional analogue thereof, is particularly useful for increasing the rate of wound healing without causing inappropriate scarring or fibrosis.

We have established that LAP, and functional analogues thereof, increases the rate of wound healing of a variety of wounds including acute wounds (such as penetrative injuries, burns, nerve damage or even wounds resulting from elective surgery). It is however preferred that LAP is used for the treatment of chronic wounds. Examples of such chronic wounds are diabetic, venous or decubitus ulceration. A preferred use of LAP is also for generally healing compromised individuals (for example the elderly).

It will be appreciated that certain amino acids of endogenously expressed LAP may be readily modified, substituted or deleted without destroying the functional characteristics of the LAP peptide. Therefore functional analogues of LAP may be conveniently used according to the invention. These analogues are generally those which when bound to a member of the TGF-β superfamily cause said member to revert to a latent state and protect the TGF-β from proteolytic degradation and/or clearance. Examples of such analogues are genetically modified mutations of LAP which retain the TGF-β binding characteristics of endogenous LAP or chemical modifications of endogenous LAP. Other analogues are chemically synthesised compounds with similar binding affinities for members of the TGF-β superfamily as that of LAP. Functional analogues referred to herein also include fragments of LAP which retain the binding affinity of LAP for members of the TGF-β superfamily.

It will also be appreciated that LAPs derived from different members of the TGF-β superfamily may exhibit variations in their amino acid sequences but still retain the functional characteristic that they may bind to a member of the TGF-β superfamily and cause said member to revert to a latent state. Each of these LAPs may be used according to the invention.

LAP or protein analogues thereof for use according to the invention may be obtained from tissues or cells grown in culture which express at least one member of the TGF-β superfamily. Preferably the tissues or cells express a TGF-β and most preferably TGF-β1 or TGF-β2.

Alternatively LAP or protein analogues thereof may be obtained from cells that have been genetically engineered to express LAP or protein analogues thereof (for instance as disclosed in WO 91/08291) or from a transgenic animal genetically engineered to express LAP or protein analogues thereof. Ideally the transgenic animal secretes LAP or protein analogues thereof. For instance transgenic mammals may secrete LAP, or protein analogues thereof, in their milk.

It is preferred that recombinant LAP from genetically engineered cells is used according to the invention because sufficient quantities of LAP for therapeutic use may be conveniently generated from such a source. This recombinant LAP may have the same amino acid sequence as endogenously occurring LAP. Alternatively. LAP may be modified as required. For example, Cys33 of LAP may be mutated to a serine residue to prevent the formation of undesirable disulphide bridges.

The medicament of the invention may take a number of different forms depending, in particular on the manner in which the medicament is to be used. Thus, for example, the medicament may be in the form of a liquid, ointment, cream, gel, hydrogel, powder, aerosol or an implantable device (e.g. by conjugation to a biopolymer (collagen or proteoglycan) sponge.

It is preferred that the medicaments are for topical application. The medicament may be most suitably used for topical application to the skin or wound area.

It will be appreciated that the vehicle of the medicament should be one which is well tolerated by the patient and allows release of LAP, or a functional analogue thereof, to the wound. The vehicle will ideally be sterile and may be combined with excipients and/or stabilizers as well as LAP, and functional analogues thereof, to form the medicament. Such a vehicle is preferably biodegradeable, bioresolvable, bioresorbable and/or non-inflammatory.

The medicament may be used in a number of ways. Thus, for example, it may be applied in, and/or around a wound of a patient to provide the desired promotion of wound healing. If the composition is to be applied to an "existing" wound, then the pharmaceutically acceptable vehicle will be "mild" enough such that it does not cause an inflammatory response or is toxic to the tissue.

The medicament may be provided on a sterile dressing or patch which may be used to cover or even pack a wound to be treated.

The medicament may be provided as an implantable device from which it may be released better. For instance, it may be released by biological dissolution or degradation of the device. Alternatively an external stimulus, such as ultrasound, may cause release of the Latency Associated Peptide or functional analogue thereof from the implant. The medicament may also be incorporated into an implant device to remain active in situ (e.g. by conjugation of the device using a suitable linker).

The medicament may be used in a range of internal wound healing applications. Thus for example, the composition may be formulated for inhalation for use in wound healing of the lungs or may be applied to internal organs for the promotion of healing of internal injuries (e.g. of the liver or bowel).

It is also possible to use medicaments in accordance with the invention in a prophylactic manner. For instance, the medicament may be applied prior to surgery so as to provide for regulation of healing of the subsequently formed surgical wound. In this case the vehicle of the composition will need to be one capable of going across the keratinous layer of the skin. Examples of suitable vehicles for this purpose include dimethyl sulphoxide and acetic acid. Alternatively the medicament may be administered prophylactically before wounding by intradermal injection. Administration by injection is particularly suited when the Latency Associated Peptide or functional analogue thereof is LAP itself or some other protein analogue.

It will be appreciated that the amount of LAP, or functional analogue thereof, required to increase the rate of wound healing depends on a number of factors such as its biological activity and bioavailability, which in turn depends on the mode of administration and the physicochemical properties of the LAP, or functional analogue thereof. Other factors include:

A) The specific condition to be treated.
B) The severity of the condition.
C) The age of the subject.
D) The site of delivery of LAP.
E) The half-life of the compound in the subject being treated.

The frequency of administration will also be influenced by the above mentioned factors and particularly the half-life of the compound within the subject being treated.

Generally, a subject being treated will derive benefit from the application of LAP, or functional analogue thereof, if it as administered to a wound within 3 days of wounding, preferably within 48 hours of wounding, more preferably within 24 hours of wounding and even more preferably within 12 hours of wounding. Ideally when the compositions are used to treat existing wounds the LAP, or functional analogue thereof should be administered as soon as the wound has occurred. Therapy with the LAP, or functional analogue thereof, should continue until the wound has healed to a clinicians satisfaction.

For acute wounds and wounds of subjects who are healing competent (e.g. the young) application of LAP, or functional analogue thereof, will ideally be at the time of wounding, preferably within 12 hours of wounding and no longer than a few days post-wounding. For chronic wounds or wounds in the healing compromised (e.g. the elderly) administration should be as soon as possible but as these wounds are long standing patients may benefit from the use of LAP days (or even weeks) after the wound first formed.

When used as a prophylactic (e.g. before surgery) the LAP, or functional analogue thereof, should be administered as soon as it is recognised that a wound may occur and particularly when there is a risk of a poor rate of wound healing (as may be the case in elderly subjects). For instance, a cream or ointment containing LAP, or functional analogue thereof may be applied to a site on the skin of a subject where elective surgery is to be performed and an increased rate of wound healing is subsequently desired. In this case, the composition may be applied during the preoperative preparation of the subject or it may even be desirable to apply the composition in the hours or days preceding the surgery (depending upon the health status and age of subject as well as the size of the wound to be formed).

Frequency of administration will depend upon the biological half-life of the compound used. Typically a cream or ointment containing LAP, or functional analogue thereof should be administered to a target tissue such that the concentration of the compound at the wound site is maintained at a level suitable for having a therapeutic effect. This may require administration daily or even several times daily.

Known procedures, such as those conventionally employed by the pharmaceutical industry (e.g. in vivo experimentation, clinical trials etc), may be used to establish specific formulations of compositions and precise therapeutic regimes (such as daily doses of the compounds and the frequency of administration).

Generally, for use in accordance with the invention a medicament containing an amount of 1 ng to 10 mg of LAP, more preferably 1 $\mu$g to 1 mg of LAP, may be applied per centimetre of linear wound. Purely by way of example, a medicament containing 5 $\mu$g LAP is suitable for application to a 1 cm linear incisonal wound. Higher doses are required to stimulate the healing of chronic wounds compared to acute wounds.

Efficacy of medicaments, and particularly those formulated for application to chronic wounds, have enhanced efficacy when combined with a protease inhibitor (e.g. galadrin) Protease inhibitors prevent or retard the degradation of the applied LAP, or functional analogue thereof, by proteases which may be found in high levels in wounds, particularly chronic wounds. The protease inhibitor is preferably a broad spectrum protease inhibitor.

It will be appreciated that LAP may be used in combination with other wound healing agents or followed by another agent (e.g. for prevention of scarring).

A preferred means of using a protein or peptide of LAP is to deliver the compound to the wound by means of gene therapy. Therefore according to a third aspect of the present invention there is provided a delivery system for use in a gene therapy technique, said delivery system comprising a DNA molecule encoding for a LAP, or functional peptide analogue thereof, which modulates wound healing, said DNA molecule being capable of being transcribed to lead to the expression of said LAP, or functional peptide analogue thereof.

According to a fourth aspect of the present invention there is provided the use of a delivery system as defined in the preceding paragraph for use in the manufacture of a medicament for increasing the rate of wound healing.

According to a fifth aspect of the present invention there is provided a method of increasing the rate of wound healing comprising administering to a patient in need of treatment a therapeutically effective amount of a delivery system as defined for the third aspect of the invention.

The delivery systems are highly suitable for achieving sustained levels of a LAP, or functional peptide analogue thereof, at a wound site over a longer period of time than is possible for most conventional delivery systems. LAP, or functional peptide analogue thereof, may be continuously expressed from cells at the wound site that have been transformed with the DNA molecule of the third aspect of the invention. Therefore, even if the LAP, or functional peptide analogue thereof, has a very short half-life as an agent in vivo, therapeutically effective amounts may be continuously expressed from the treated tissue.

Furthermore, the delivery system of the invention may be used to provide the DNA molecule (and thereby the LAP, or functional peptide analogue thereof which is an active therapeutic agent) without the need to use conventional pharmaceutical vehicles such as those required in ointments or creams that are contacted with the wound. This is particularly beneficial as it can often be difficult to provide a satisfactory vehicle for a compound for use in wound healing (which are required to be non-inflammatory, biocompatible, bioresorbable and must not degrade or inactivate the active agent (in storage or in use)).

The delivery system is such that the DNA molecule is capable of being expressed (when the delivery system is administered to a patient) to produce LAP, or functional peptide analogue thereof, which has activity for wound healing.

The DNA molecule may be contained within a suitable vector to form a recombinant vector. The vector may for example be a plasmid, cosmid or phage. Such recombinant vectors are highly useful in the delivery systems of the invention for transforming cells with the DNA molecule.

Recombinant vectors may also include other functional elements. For instance, recombinant vectors can be designed such that the vector will autonomously replicate in the nucleus of the cell. In this case, elements which induce DNA replication may be required in the recombinant vector. Alternatively the recombinant vector may be designed such that the vector and recombinant DNA molecule integrates into the genome of a cell. In this case DNA sequences which favour targeted integration (e.g. by homologous recombination) are desirable. Recombinant vectors may also have DNA coding for genes that may be used as selectable markers in the cloning process.

The recombinant vector may also further comprise a promoter or regulator to control expression of the gene as required.

The DNA molecule may (but not necessarily) be one which becomes incorporated in the DNA of cells of the subject being treated. Undifferentiated cells may be stably transformed leading to the production of genetically modified daughter cells (in which case regulation of expression in the subject may be required e.g. with specific transcription factors or gene activators). Alternatively, the delivery system may be designed to favour unstable or transient transformation of differentiated cells in the subject being treated. When this is the case, regulation of expression may be less important because expression of the DNA molecule will stop when the transformed cells die or stop expressing the protein (ideally when the wound, fibrosis or scarring has been treated or prevented).

The delivery system may provide the DNA molecule to the subject without it being incorporated in a vector. For instance, the DNA molecule may be incorporated within a liposome or virus particle. Alternatively the "naked" DNA molecule may be inserted into a subject's cells by a suitable means e.g. direct endocytotic uptake.

The DNA molecule may be transferred to the cells of a subject to be treated by transfection, infection, microinjection, cell fusion, protoplast fusion or ballistic bombardment. For example, transfer may be by ballistic transfection with coated gold particles, liposomes containing the DNA molecule, viral vectors (e.g. adenovirus) and means of providing direct DNA uptake (e.g. endocytosis) by application of plasmid DNA directly to the wounded area topically or by injection.

Whilst the above considerations mainly apply to wounds of man it will be appreciated that wound healing, can also be problematic in other animals (especially veterinary and domestic animals such as cattle, horses, dogs, cats etc). For instance, abdominal wounds or adhesions are a major reason for having to put down horses. The medicaments and delivery systems discussed above are also suitable for use in the healing of such animals.

The present invention will now be further described with reference to the following non-limiting example.

EXAMPLE

The effect of LAP on wound healing was assessed using a rat model.

1. Methods

Full details of the experimental procedures described below, which are all conventional are given in Shah et al. (1994) J. Cell Sci. 107 p1137–1157. Briefly, the following experimental steps were taken:

Adult male Sprague-Dawley rats weighing 225–250 g were anaesthetised by halothane, nitrous oxide and oxygen inhalation. Four full-thickness, linear incisions, 1 cm in length, down to and including the panniculus carnosus were made on the dorsal skin of the animal. The incisions were placed equidistant from the midline and adjacent to the four limbs.

One of the wounds was left unmanipulated as a control. Two wounds were injected intradermally with 100 $\mu$l (50 $\mu$l down each wound margin) of phosphate buffered saline containing recombinant LAP (0.04 $\mu$g, 0.4 $\mu$g or 4.0 $\mu$g). The fourth wound was injected intradermally with an equivalent volume (100 $\mu$l–50 $\mu$l down each wound margin) of the vehicle in which LAP was dissolved (phosphate buffered saline) as a sham control. Animals were injected just before wounding, 24 and 48 hours later.

Animals were killed and the wounds were harvested at the following times post wounding: 2 hours, 3 hours, 12 hours, 24 hours, 4 days, 7 days, 40 days and 80 days. At each time point there were at least 4 rats per treatment (i.e. n=at least 4 for each dose of LAP used).

Wounds were processed for routine histology by fixation, wax embedding, sectioning and staining. Alternatively wounds were processed for immunocytochemistry by embedding in OCT compound, freezing in liquid nitrogen, cryosectioning and immunostaining with a variety of antibodies to detect TGF-$\beta$1, TGF-$\beta$2, TGF-$\beta$3, TGF-$\beta$ receptor type II, fibronectin, collagen, monocytes and macrophages, etc.

Histological and immunocytochemical preparations were studied carefully for the effect of LAP on wound healing (especially any anti-scarring effect as would be expected from the prior art). Particular attention was paid to the organisation and orientation of collagen and extracellular matrix molecules deposited at the wound site.

2. Results

None of the treatments resulted in an anti-scarring effect. At 80 days and 40 days post wounding the LAP treated wounds were no different from controls in terms of scar quality or quantity.

Surprisingly, however, at the earlier time points post wounding the LAP treated wounds showed a number of differences from control or sham control wounds. In all cases, these responses were dose dependant, i.e. the least effect was seen at the dose of 0.04 $\mu$g LAP and the highest effect at 4 $\mu$g of LAP.

There was a dose dependant increase in inflammatory cells (monocytes and macrophages) in the LAP treated wounds. Likewise there was a dose dependent increase in fibronectin staining within the early wound site (i.e. up to 14 days post wounding) and an increase in collagen deposition. The LAP treated wounds also showed fibronectin and collagen deposition, as well as inflammatory cells earlier than was seen in the control wounds. Interestingly from 3 hours post wounding until 14 days post wounding the LAP treated wounds showed a dose dependent increase in staining for the TGF$\beta$ type I receptor and type II receptor. This elevated staining for the TGF$\beta$ receptor is different from that present in control or sham control wounds. In PBS treated sham control wounds, TGF$\beta$ receptor I staining increased at 3 hours post wounding, but then decreased within 24 hours post wounding. In unmanipulated wounds there was no early increase in TGF$\beta$ receptor staining at the wound site. By contrast the LAP treated wounds showed a dose dependent increase in TGF$\beta$ receptor staining which stayed elevated for 14 days post wounding.

The LAP treated wounds also showed a dose dependent decrease in staining for TGF$\beta$3 at the wound site. This decrease in TGF$\beta$3 staining compared to control and sham control wounds was most marked at 24 hours and 4 days post wounding.

All of these effects (noted above) with the exogenous addition of the LAP, i.e. increase in inflammatory cells, particularly monocytes and macrophages, increase in extracellular matrix deposition, e.g. fibronectin and collagen, increase in TGF$\beta$ receptor staining are identical to effects observed when exogenous TGF$\beta$1 itself is added to the wound.

Furthermore, wound healing was accelerated in a dose dependant fashion in the LAP treated wounds, using a number of parameters (e.g. completion of epithelialisation, maturation of the granulation tissue or early deposition of collagen). Therefore exogenous addition of LAP has the same effect on wound healing as has been reported for exogenous addition of TGF$\beta$1.

These findings are not at all what might be predicted from the prior art which teaches that exogenous LAP neutralises TGF$\beta$1 and hence would be expected to have anti-scarring activity. Instead it acts like exogenous addition of TGFβ1 and increasing the rate of wound healing, but has no anti-scarring activity.

Exogenous addition of LAP therefore has value in stimulating the healing of wounds. LAP is particularly useful for chronic wounds (such as venous ulcers, diabetic ulcers, pressure sores, etc.), as well as acute surgical incisions.

What is claimed is:

1. A method of increasing the rate of wound healing comprising administering to a subject in need of treatment a therapeutically effective amount of Latency Associated Peptide, or a peptide analogue thereof that is capable of maintaining a Transforming Growth factor β in a latent state, wherein the Latency Associated Peptide, or a peptide analogue thereof, is not co-administered with Transforming Growth factor β.

2. The method according to claim 1 wherein the Latency Associated Peptide, or peptide analogue thereof, is capable of maintaining Transforming Growth factor β1 and/or Transforming Growth factor β2 in a latent state.

3. The method according to claim 1 wherein the wound is an acute wound.

4. The method according to claim 3 wherein the acute wound is one selected from the group consisting of a penetrative injury, a burn, nerve damage, a wound resulting from surgery or a wound of an internal organ.

5. The method according to claim 1 wherein the wound is a chronic wound.

6. The method according to claim 5 wherein the chronic wound is selected from the group consisting of diabetic, venous or decubitus ulcerations.

7. The method according to claim 1 wherein the subject is a healing compromised individual.

8. The method according to claim 7 wherein the healing compromised individual is an elderly human or animal.

9. The method according to claim 1 wherein Latency Associated Peptide, or a peptide analogue thereof is incorporated in a medicament that is in the form of a liquid, ointment, cream, gel, hydrogel, powder, aerosol or implant.

10. The method according to claim 9 wherein the medicament contains from 1 ng to 10 mg of Latency Associated Peptide or peptide analogue thereof.

11. The method according to claim 9 wherein the medicament is for topical application.

12. The method according to claim 1 wherein a peptide analogue of Latency Associated Peptide is used which is a chemical or genetically engineered modification of Latency Associated Peptide or a chemically synthesised peptide analogue of Latency Associated Peptide.

13. The method according to claim 1 wherein the Latency Associated Peptide or peptide analogue thereof is obtained from cells genetically engineered to express said Latency Associated Peptide or peptide analogue thereof.

14. A method of increasing the rate of dermal wound healing comprising topically administering to the skin of a subject in need of treatment a therapeutically effective amount of a DNA molecule encoding for a Latency Associated Peptide, or peptide analogue thereof, which is capable of maintaining a Transforming Growth Factor β in a latent state, said DNA molecule being capable of being transcribed to lead to the expression of said Latency Associated Peptide, or peptide analogue thereof, and wherein said DNA molecule is used without being incorporated in a vector.

* * * * *

UNITED STATES PATENT AND TRADEMARK OFFICE
CERTIFICATE OF CORRECTION

PATENT NO. : 6,319,907 B1
DATED : November 20, 2001
INVENTOR(S) : Ferguson

It is certified that error appears in the above-identified patent and that said Letters Patent is hereby corrected as shown below:

<u>Title page,</u>
Item [57], ABSTRACT,
Please replace to read as follows:

-- [57]                              ABSTRACT

The present application relates to the use of Latency Associated Peptide, or a functional analogue thereof, for the treatment of wounds such that the rate of wound healing is increased. Preferred agents for use in such treatments include Latency Associated Peptide isolated from cells expressing the same and peptide functional analogues of Latency Associated Peptide. --

Signed and Sealed this

Twenty-fourth Day of December, 2002

JAMES E. ROGAN
*Director of the United States Patent and Trademark Office*